(12) United States Patent
Nabatova-Gabain et al.

(10) Patent No.: US 7,167,242 B2
(45) Date of Patent: Jan. 23, 2007

(54) SAMPLE ANALYSIS METHOD

(75) Inventors: Nataliya Nabatova-Gabain, Kyoto (JP); Seiichi Hirakawa, Kyoto (JP); Yoko Wasai, Kyoto (JP)

(73) Assignee: Horiba, Ltd., Kyoto (JP)

( * ) Notice: Subject to any disclaimer, the term of this patent is extended or adjusted under 35 U.S.C. 154(b) by 68 days.

(21) Appl. No.: 11/089,783

(22) Filed: Mar. 25, 2005

(65) Prior Publication Data

US 2005/0219529 A1 Oct. 6, 2005

(30) Foreign Application Priority Data

Mar. 30, 2004 (JP) ............................. 2004-101357

(51) Int. Cl.
*G01J 4/00* (2006.01)
(52) U.S. Cl. ..................................... 356/369
(58) Field of Classification Search ...................... None
See application file for complete search history.

(56) References Cited

U.S. PATENT DOCUMENTS 4,332,833 A * 6/1982 Aspnes et al. .................. 427/8

6,808,742 B2 * 10/2004 Rouse et al. .................. 427/162

FOREIGN PATENT DOCUMENTS

| JP | 2002-340528 | 11/2002 |
|---|---|---|
| JP | 2002-340789 | 11/2002 |

* cited by examiner

*Primary Examiner*—Tu T. Nguyen

(57) ABSTRACT

A sample, in which a dielectric film having a dielectric constant equal to or larger than 50 (based on electrical measurement) is formed on a substrate, is measured by an ellipsometer while a model corresponding to the sample is formed based on effective medium approximation (EMA). A film corresponding to the dielectric film of the model includes void volume fraction between 60% and 90%. A calculated value based on the model is compared with a value measured by the ellipsometer and fitting is applied to decrease a difference between the compared values in order to specify the thickness and the optical constant of the sample.

20 Claims, 10 Drawing Sheets

FIG. 7

| $X^2$ | 6.572140 |
|---|---|
| THICKNESS (Å) | 918.391±7.803 |
| PZT (%) | 28.676±0.088 |
| PZT ($\varepsilon s$) | 372.788±23.339 |
| PZT ($\omega t$) | 2.698±0.063 |
| PZT ($\Gamma_0$) | 0.243±0.012 |

SAMPLE ANALYSIS METHOD

CROSS-REFERENCE TO RELATED APPLICATIONS

This Nonprovisional application claims priority under 35 U.S.C. §119(a) on Patent Application No. 2004-101357 filed in Japan on Mar. 30, 2004, the entire contents of which are hereby incorporated by reference.

BACKGROUND OF THE INVENTION

The present invention relates to a sample analysis method which enables analyzing a sample provided with a dielectric film formed of a ferroelectric substance or a high-dielectric constant substance, by an ellipsometer in overall optical range by forming a model including a great amount of void based on effective medium approximation.

Conventionally, an ellipsometer has been used for analyzing information on a sample. An ellipsometer is designed to obtain a phase difference (Δ: delta) and an amplitude ratio (Ψ: psi) by applying polarized light to a sample and measuring a difference between a polarization state of the incident light and that of the reflected light. The sample to be analyzed includes a simple substrate, a substrate having a film formed thereon, and the like.

FIG. 9 is a graph showing the measurement result, of a sample provided with a silicon dioxide film formed on a silicon substrate, by an ellipsometer. The abscissa axis denotes the wavelength (nm: nanometer) of the incident light into the sample, the right ordinate axis denotes the measured phase difference (Δ: delta), and the left ordinate axis denotes the measured amplitude ratio (Ψ: psi). It should be noted that, when the wavelength of the incident light is 633 nm, the dielectric constant of the silicon dioxide film, based on optical measurement, is approximately 2.1.

A single combination of a refractive index (n), an extinction coefficient (k) and a thickness (d) of a film cannot be obtained directly from a phase difference and an amplitude ratio of a sample measured by an ellipsometer as described above. Accordingly, in order to obtain the single combination of the refractive index, the extinction coefficient and the thickness of a film from the measured phase difference and amplitude ratio, formation of a model, based on some combinations (n, k, d), corresponding to the sample and comparison between a phase difference and an amplitude ratio obtained theoretically from the model and a phase difference and an amplitude ratio measured by an ellipsometer are performed in addition to the measurement using the ellipsometer. It should be noted that the formation of a model includes setting of conditions corresponding to the physical properties of the sample, and the items of the conditions to be set include the material of the substrate and the film, the thickness of each film layer, and the optical constants of the substrate and the film. Moreover, used usually for setting each item are a known reference corresponding to the sample, a required dispersion formula which represents the wavelength dependence of the dielectric constant and has a plurality of parameters, or other particular matters.

Furthermore, a process (which will be referred to as fitting) is performed to change the parameters of the dispersion formula, the thickness of each film layer of the model, or other matters so that the degree of the difference between the both to be obtained from the above comparison becomes minimal. As a result of fitting of the difference between the both, usually obtained by calculation using the least squares method, is determined that the result obtained by the least squares method, has become relatively small, the refractive index and the extinction coefficient of the film are obtained from the values of the parameters of the dispersion formula, and the thickness is specified as the thickness of the film in the sample. It should be noted that the formation of a model, the calculation which uses the least squares method, the fitting and the like are generally performed manually or automatically based on a desired program using a computer (see Japanese Patent Application Laid-Open No. 2002-340789 and Japanese Patent Application Laid-Open No. 2002-340528).

The analysis method described above can be performed without trouble when the boundary between a substrate S1 and a film S2, which constitute a sample S as shown in FIG. 10A, is flat, the film S2 is smooth and the substance constituting the film S2 is homogeneous and continuous. However, since an actual sample S has roughness on the surface of the film S2 as shown in FIG. 10B, a favorable result may not be obtained by performing the above analysis method without modification, depending on the degree of the roughness.

Accordingly, in such a case, a model is formed using an idea of effective medium approximation which substitutes the film S2 having roughness shown in FIG. 10B with a first film S2a, which is formed of a homogeneous and continuous substance of the film S2 and has a thickness d1, and a second film S2b, which is formed of a substance M of the film S2 including a desired ratio of void V (percentage of void, which will be referred to as a void) and has a thickness d2. Sample analysis is made by applying fitting to the thickness d1 of the first film S2a, the thickness d2 of the second film S2b, the volume fractions of the material M and the void in the second film S2b, and the parameters of the dispersion formula corresponding to the sample with respect to the model formed as described above.

The value of the void to be set for a model is decided based on the degree of the roughness, and the maximum value of the void is generally considered to be approximately 40~55% in view of the range which enables formation of a film and often is set to be 50%. It should be noted that, when it is unknown whether the film surface of the sample has roughness or not, it is generally determined whether roughness exists or not by performing both analyzing methods, one which uses effective medium approximation mentioned above, and another which does not use effective medium approximation, and judging which analyzing method gives a result more highly compatible to an actual sample, using the calculation result of least squares method.

Moreover, the effective medium approximation is applied not only to a layer of a case where the film surface of a sample has roughness, but also to a boundary layer of a case where the boundary between a substrate and a film or the boundary between film layers has roughness. Furthermore, the effective medium approximation may be used for decreasing the value of the refractive index as a technique for actually making the analysis, regardless of existence of roughness. In this case, whether effective medium approximation is to be used or not is also judged by determining the result of analysis using a model including void based on the effective medium approximation.

For example, assume an analysis of a sample in which a first film made of amorphous silicon is formed on a glass substrate and a second film made of a native oxide film is formed on the first film. Further assume that the calculation result of the least squares method (which corresponds to the mean square error $\chi^2$) becomes 16.6 when the thickness of the first film of this sample is first set to be 2,000 angstroms, the thickness of the second film is set to be 20 angstroms, a model is formed using a known amorphous silicon reference and fitting is applied to this model.

Next, assume that the calculation result of the least squares method becomes 10.6 and the volume fraction of amorphous silicon in the first film becomes approximately 86% when the thickness of the first film and the thickness of the second film are set to be the same as those described above, the volume fraction of amorphous silicon in the first film is set to be 50% and the void of the first film is set to be 50% using the effective medium approximation regardless of roughness, a model is formed using a known amorphous silicon reference and fitting is applied in the same manner as described above. Since a smaller value of the calculation result of the least squares method is preferable, it is found that the result of analysis (result of fitting) obtained by using a known reference and by forming a model including void based on effective medium approximation is more preferable than that of the first case.

Finally, assume that the thickness of the first film and the thickness of the second film are set to be the same as those of the first case, the volume fraction of amorphous silicon in the first film is set to be 86% and the void of the first film is set to be 14% using the effective medium approximation regardless of roughness in view of the volume fraction of amorphous silicon of the second case, a model is formed using not the reference but a dispersion formula and fitting is applied in the same manner as described above. When the calculation result of the least squares method is 0.14 and the volume fraction of amorphous silicon in the first film is approximately 99.16%, it is found that there is no point in formation of a model including void since the void is approximately 0%, although the calculation result of the least squares method is extremely preferable. Accordingly, in such a case, analysis is generally made by forming a model including no void and using a dispersion formula.

A conventional analysis method based on optical measurement using an ellipsometer has a problem that the physical properties of a sample cannot be analyzed based on the complex dielectric constant since the complex dielectric constant may not be obtained in a desired optical range when the sample is provided with a high-dielectric constant film or a ferroelectric film having a dielectric constant equal to or larger than 50 based on electrical measurement.

That is, a range of a conventional analysis method which uses an ellipsometer, is often 248 nm~826 nm inside overall optical range of light wavelengths (DUV (Deep Ultraviolet) ~NIR (Near Infrared): 190 nm~1700 nm, which corresponds to 0.75 eV~6.5 eV of a photon energy range. Each of a high-dielectric constant substance and a ferroelectric substance has three parts of electric polarizability: electric polarizability, ionic polarizability and dipole polarizability. From the optical measurements, it is known that refractive index and extinction coefficient of the ferroelectric and high-dielectric constant substances have a steep peak below 400 nm. However, it is generally considered that the dispersion formula and the reference which can deal with such a sharp data have not been found yet. Accordingly, the fact is that we cannot find any biblio, document or the like which correctly defines how the refractive index and the extinction coefficient of a high-dielectric constant substance and a ferroelectric substance change in the optical range under 400 nm (range of 248 nm~400 nm). It should be noted that electrical measurement used for measuring a dielectric constant is within a frequency range of 100 kHz~1 MHz far out of a near-infrared range included in the optical measurement range, and the measurement range of electrical measurement and that of optical measurement are completely different from each other.

Moreover, since the dielectric constant of a sample varies according to the measurement range, the problem described above arises in an optical measurement range under 400 nm. Accordingly, physical properties analysis of a high-dielectric substance or a ferroelectric substance in an optical measurement range under 400 nm should be made using another apparatus which is of great price and requires analysis time.

BRIEF SUMMARY OF THE INVENTION

The present invention has been made after an earnest study for analysis of a high-dielectric constant substance and a ferroelectric substance by the present inventor with the aim of solving the above problems, and it is an object of the present invention to provide a sample analysis method capable of analyzing a high-dielectric constant substance or a ferroelectric substance even in an optical measurement range under 400 nm by forming a model using effective medium approximation regardless of existence of roughness and setting a value beyond a generally conceivable range for a void.

In order to solve the above problems, a sample analysis method according to the first aspect is characterized by comprising the steps of applying polarized light to a sample, in which a dielectric film having a dielectric constant equal to or larger than 50, based on electrical measurement, is formed on a substrate, by an ellipsometer; measuring a value of a difference between a polarization state of incident light and a polarization state of the light reflected from the sample; forming a model including void at a ratio between 60% and 90% based on effective medium approximation, setting conditions corresponding to the sample; calculating a value corresponding to the value of the difference in a polarization state measured by the ellipsometer based on the formed model; comparing the calculated value with the value of the difference measured by the ellipsometer; performing calculation using an effective medium approximation formula and a dispersion formula in the model, so that a difference between the compared values becomes minimal; and analyzing the sample based on a result of the calculation.

With the first aspect, a sample is analyzed by measuring with an ellipsometer a sample provided with a high-dielectric constant film or a ferroelectric film having a dielectric constant equal to or larger than 50, based on electrical measurement, and forming a model including void at a ratio between 60% and 90% based on effective medium approximation in a film corresponding to a dielectric film. Such void volume fraction, between 60% and 90%, is a value which makes film formation difficult from a physical standpoint and is generally not set. However, when a value in a range mentioned above is still set, it becomes possible to mathematically apply fitting, which can deal with a measurement result having a steep peak, to a sample provided with a high-dielectric constant film or a ferroelectric film and to analyze a sample even in the range under 400 nm, which is conventionally impossible, due to very steep increase in optical constants.

With the invention by the present inventors, it is found that a difference obtained by the least squares method tends to be minimal by setting a void volume fraction to be in a range between 65% and 75%, and the inventor has judged that it is preferable to set a void volume fraction to be in a range between 67% and 73%, more specifically approximately 70%, to apply fitting effectively.

The sample analysis method according to the second aspect is characterized in that the dispersion formula includes parameters describing a wavelength dependence of a dielectric constant of any dielectric film in the sample in which a stack of films is formed, corresponding to an optical measurement range, to analyze a dielectric constant in the optical measurement range, based on values of the parameters of the dispersion formula describing the dielectric constant.

With the second aspect, a dielectric constant in an optical measurement range under 400 nm of a dielectric film having a dielectric constant equal to or larger than 50, based on electrical measurement, can be specified by reference to a set of the parameter's values in a dispersion formula. As a result, a conventional physical properties analysis which uses another apparatus which is of high cost and time-consuming can be eliminated and physical properties analysis for a high-dielectric constant substance or a ferroelectric substance based on the specified dielectric constant can be made more rapidly and easily than conventional technique.

With the first aspect, a sample can be analyzed even in an optical measurement range under 400 nm, which is conventionally impossible, by forming a model including void at a volume fraction between 60% and 90% based on effective medium approximation with respect to a sample provided with a dielectric film having a dielectric constant equal to or larger than 50 based on electrical measurement and applying fitting to a value measured by an ellipsometer.

Moreover, with the second aspect, physical properties of a sample, provided with a dielectric film having a dielectric constant equal to or larger than 50, based on electrical measurement, can be analyzed by obtaining a dielectric constant in an optical measurement range under 400 nm, and the cost, time, trouble or other conditions required for physical properties analysis of the sample (based on the dielectric constant) can be drastically improved as compared to conventional technique.

The above and further objects and features of the invention will more fully be apparent from the following detailed description with accompanying drawings.

BRIEF DESCRIPTION OF THE SEVERAL VIEWS OF THE DRAWINGS

FIG. 4 is a schematic diagram showing a setting menu of the thickness of a film, void and the like;

FIG. 7 is a diagram showing a result associated with fitting;

DETAILED DESCRIPTION OF THE INVENTION

The following description will explain the present invention in detail with reference to the drawings illustrating an embodiment thereof.

Figure 1:
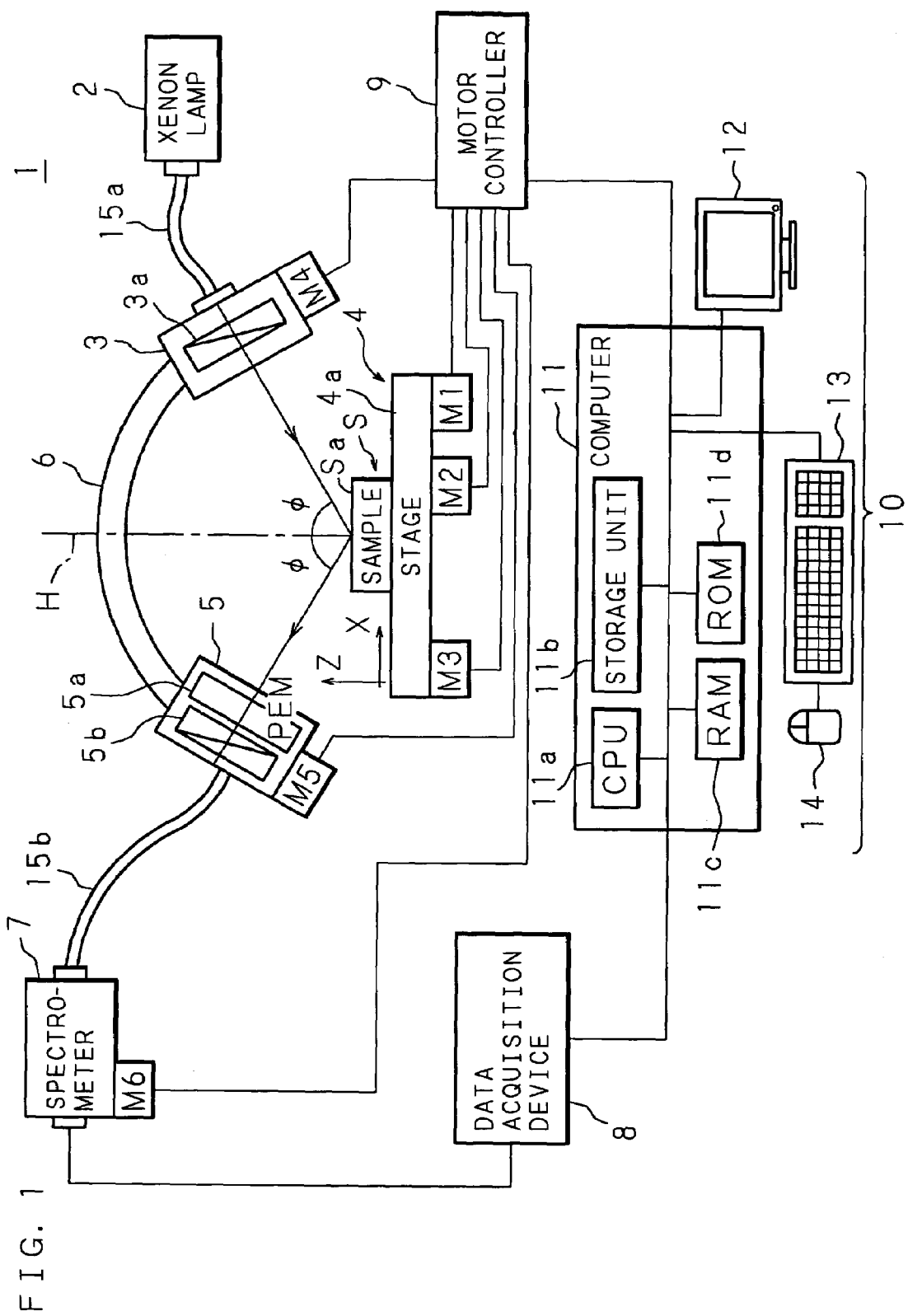
FIG. 1 is a schematic diagram showing the configuration of an ellipsometer and a computer to be used in a sample analysis method according to the present invention.
Figure 2A:
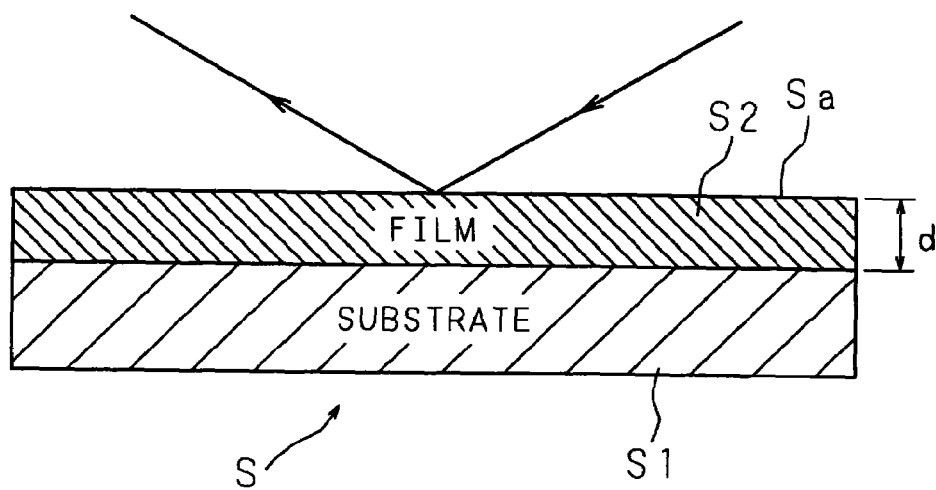
FIG. 2A is a sectional view of the sample.

FIG. 1 is a schematic diagram showing the entire configuration of an ellipsometer 1 and a computer 10 to be used in a sample analysis method according to an embodiment of the present invention. The ellipsometer 1 applies polarized light to a sample S, in which a film S2 is formed on a substrate S1 as illustrated in FIG. 2A, and measures a phase difference $\Delta$ and an amplitude ratio $\Psi$ of that light on the basis of a difference between a polarization state of the incident light and a polarization state of reflected light. The present invention is to analyze a sample S, in which a film S2 of a ferroelectric substance or a high-dielectric constant substance, having a dielectric constant equal to or larger than 50 (based on electrical measurement) is formed, including, in addition to the structure illustrated in FIG. 2A, a sample in which a stack of films is formed on a substrate S1 and at least one of the films is formed of a ferroelectric substance or a high-dielectric constant substance.

The computer 10 is designed to: form a model corresponding to the sample using a dispersion formula, a reference and the like; obtain a phase difference and an amplitude ratio from the model; apply fitting by comparing the calculated phase difference and the amplitude ratio with a phase difference and an amplitude ratio measured by the ellipsometer 1; and analyze a thickness of the film, a refractive index and an extinction coefficient as optical constants of the film, and a complex dielectric constant. The computer 10 according to this embodiment applies fitting by forming a model provided with a dielectric film including void at a ratio between 60% and 90%, using effective medium approximation (EMA).

First, the structure of the ellipsometer 1 illustrated in FIG. 1 will be explained by way of example of an ellipsometer which can be used in the present invention. In the ellipsometer 1, a xenon lamp 2 and a light polarizer 3 are connected with each other via a first optical fiber cable 15a to apply polarized light to the sample S laid on a stage 4 and to receive light reflected from the sample S with a light receiver 5. The light receiver 5 is connected with a spectrometer 7 via a second optical fiber cable 15b, and the spectrometer 7 measures the polarization state of light received by the light receiver 5 at each wavelength. The spectrometer 7 transmits an analog signal representing the measured polarization state to a data acquisition device 8, and the data acquisition device 8 converts the analog signal into a desired value and transmits the measured values obtained by the ellipsometer 1 to the computer 10.

The stage 4, the light polarizer 3, the light receiver 5 and the spectrometer 7 are respectively provided with a first motor M1~a sixth motor M6, drive of which is respectively controlled by a motor controller 9 connected with the computer 10. It should be noted that the motor controller 9 controls the respective motors M1~M6 based on an instruction outputted from a CPU 11a of the computer 10.

The xenon lamp 2 of the ellipsometer 1, which is a source of white light including a number of wavelength components, sends generated white light to the light polarizer 3.

The light polarizer 3 is disposed on an arcuate rail 6, has a polarizer 3a therein, polarizes white light with the polarizer 3a and applies the light to the sample S. The light polarizer 3 is driven by a fourth motor M4 to move along the rail 6 so as to adjust an angle (angle of incidence φ) of incident light with respect to a perpendicular H of the surface Sa of the sample S.

The stage 4 is driven by a first motor M1~a third motor M3 to move respectively in X and Y directions (see FIG. 1), which cross each other at 90 degrees in the stage surface 4a on which the sample S is laid, and in a Z direction corresponding to the height direction. Since the stage 4 can be moved in this manner, it becomes possible to apply light to a desirable point of the sample S in order to measure a plurality of points of the sample S.

The light receiver 5 is disposed on the rail 6 similarly to the light polarizer 3, has a PEM (Photo Elastic Modulator) 5a and an analyzer 5b incorporated therein and guides light reflected from the sample S through the PEM 5a to the analyzer 5b. The light receiver 5 is driven by a fifth motor M5 to move along the rail 6 so as to reliably catch light reflected from the sample S. Movement of the light receiver 5 is controlled by the motor controller 9 in conjunction with movement of the light polarizer 3 to an angle of reflection φ equal to an angle of incidence φ. It should be noted that the PEM 5a incorporated in the light receiver 5 obtains elliptically polarized light from linearly polarized light by applying phase modulation by a desired frequency (e.g. 50 kHz) to received light in order to improve measurement speed and measurement accuracy. The analyzer 5b transmits specific polarized light from various types of polarized light to which the PEM 5a has applied phase modulation.

Figure 3:
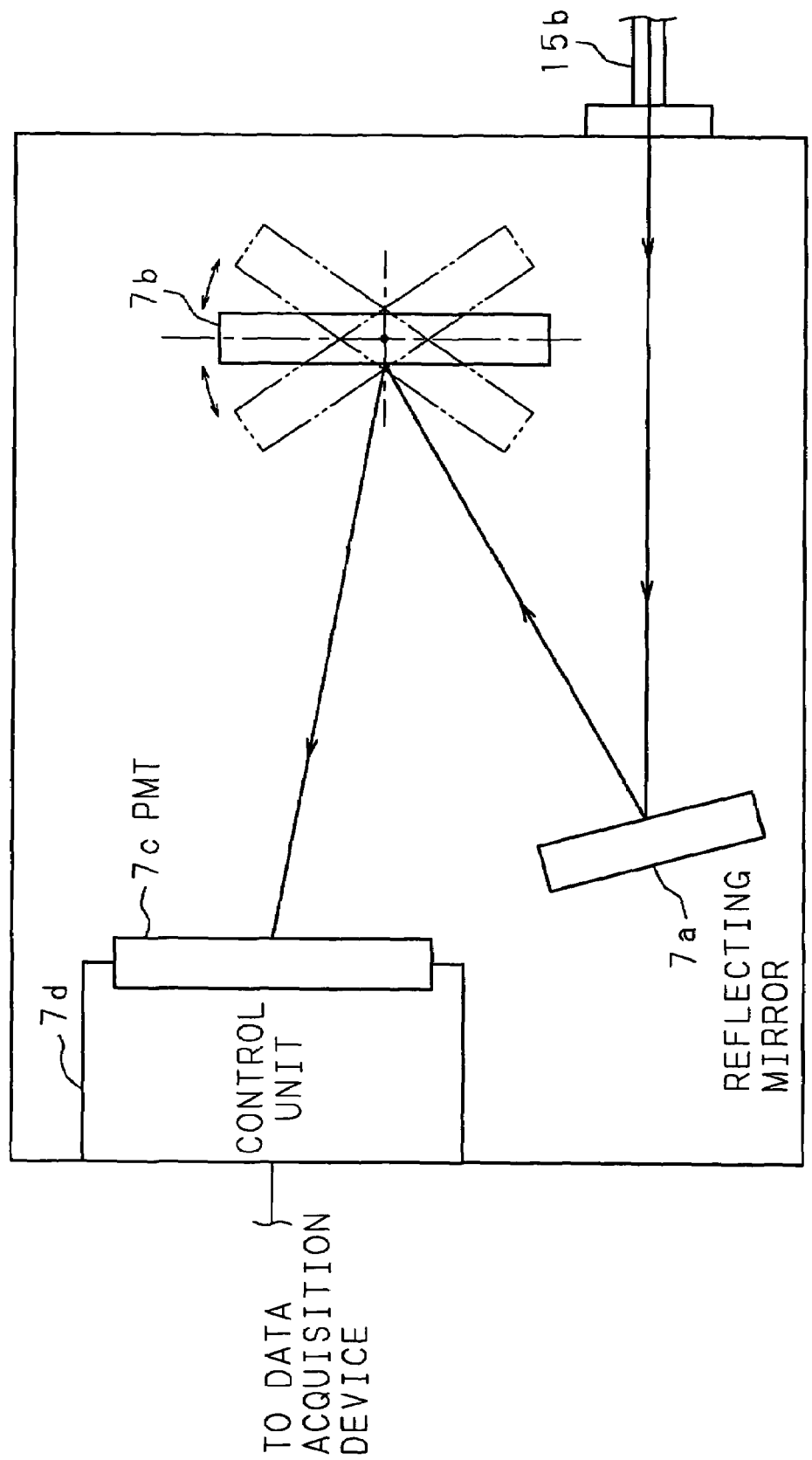
FIG. 3 is a schematic diagram showing the interior configuration of a spectrometer.

The spectrometer 7 comprises a reflecting mirror 7a, diffraction grating 7b, a photomultiplier (PMT) 7c and a control unit 7d as illustrated in FIG. 3 so as to reflect light sent from the light receiver 5 through the second optical fiber cable 15b with the reflecting mirror 7a and guide the light to the diffraction grating 7b. An angle of the diffraction granting 7b varies by means of a sixth motor M6 shown in FIG. 1, so that a wavelength of a light emitted by the diffraction granting 7b can be changed, due to the change in diffraction direction of the light guided by the angle variation. It should be noted that, although it is not shown in FIG. 3, a sine bar mechanism is linked which mechanically applies sine transform to the angle of the diffraction grating 7b and performs dial indicating in order to display the wavelength corresponding to the changed angle of the diffraction grating 7b numerically. Moreover, the spectrometer 7 may be used in a manner that the photomultiplier 7c is combined with a photodiode array (PDA).

The PMT 7c measures light emitted from the diffraction grating 7b, and the control unit 7d generates an analog signal corresponding to the measured wavelength and sends it to the data acquisition device 8. Thus, preferable measurement accuracy can be realized by the spectrometer 7 which can change the angle of the diffraction grating 7b and measures the respective wavelengths. As a result, the spectrometer 7 can measure while changing the wavelength range and increment according to the thickness of a film layer of the sample and, for example, change the wavelength in small steps when the thickness is large. Instead of the spectrometer 7, a multi channel unit can be used, which is constructed by a plurality (32, 64 or other numbers) of photo multipliers corresponding to different wavelengths and aligned in a fan-like form with respect to the diffraction granting.

The data acquisition device 8 calculates a phase difference Δ and an amplitude ratio Ψ of a polarization state (p-polarization, s-polarization) of measured reflected light based on the signal transmitted from the spectrometer 7 and sends the calculation result to the computer 10. It should be noted that the phase difference Δ and the amplitude ratio Ψ have a relation of the following expression (1) with respect to a complex Fresnel reflection coefficient Rp of p-polarized light and a complex Fresnel reflection coefficient Rs of s-polarized light:

$$Rp/Rs = \tan \Psi \cdot \exp(i \cdot \Delta) \quad (1)$$

Here, i is an imaginary unit (the same goes hereinafter). Rp/Rs is referred to as a ratio of the complex Fresnel reflection coefficients ρ.

Meanwhile, the computer 10 is composed of a computer body 11, a display 12, a keyboard 13, a mouse 14 and the like. In the computer body 11, a CPU 11a, a storage unit 11b, a RAM 11c, a ROM 11d and the like are connected via an internal bus. The CPU 11a is designed to perform various processes, which will be described later, according to various computer programs stored in the storage unit 11b. The RAM 11c temporally stores various data and the like on processes while the ROM 11d stores the contents of the function of the computer 10 and the like. It should be noted that the storage unit 11b stores, in addition to various computer programs, known data on manufacturing processes of the sample S, a plurality of dispersion formulas to be utilized for formation of a model, reference data corresponding to various samples and the like.

Figure 2B:
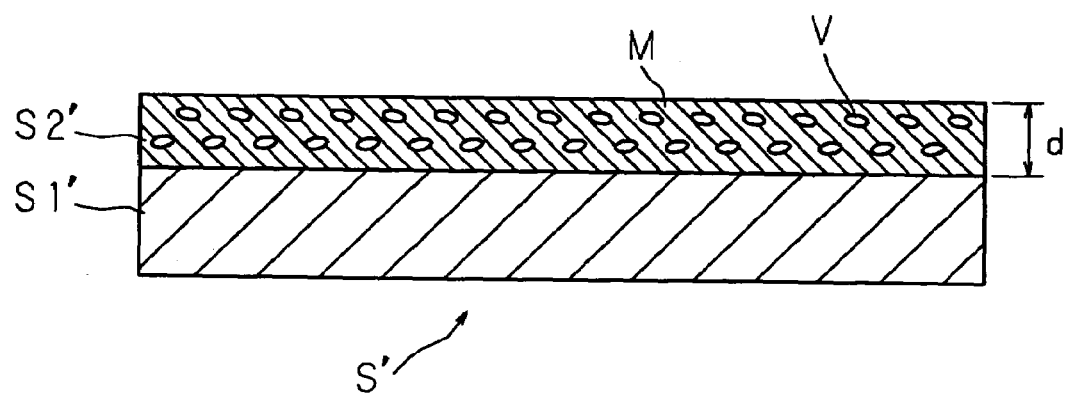
FIG. 2B is a schematic diagram showing the structure of a model including void based on effective medium approximation.

Assuming that the complex dielectric constant of the substrate S1 and the ambient of the sample S is known from the phase difference Δ and amplitude ratio Ψ transmitted from the data acquisition device 8, the computer 10 obtains the thickness d of the film S2 and the complex refractive index N of the film S2 by forming a model corresponding to the material structure of the sample S illustrated in FIG. 2A using a modeling program previously stored in the storage unit 11b. For the formation of a model in this embodiment, a model S' having a structure, in which a film S2' includes large amount of voids V (air component) in a dielectric substance M (dielectric component) having a dielectric constant equal to or larger than 50 (based on electrical measurement) is formed on a substrate S1' as illustrated in FIG. 2B, is formed using effective medium approximation regardless of existence of roughness in the sample S. It should be noted that, when n represents the refractive index of the film and k represents the extinction coefficient, the complex refractive index N can be calculated from the following optical expression (2):

$$N = n - ik \quad (2)$$

Moreover, when λ represents the wavelength of light from the light polarizer 3 of the ellipsometer 1, the phase difference Δ and amplitude ratio Ψ calculated by the data acquisition device 8 have a relation of the following expression (3) with respect to the thickness d, the refractive index n and the extinction coefficient k of the film in the sample S:

$$(d,n,k) = F(\rho) = F(\Psi(\lambda,\phi), \Delta(\lambda,\phi)) \quad (3)$$

With the use of the thickness of a film of the sample S and a dispersion formula, which represents the wavelength dependency of the complex dielectric constant and includes a plurality of parameters, the computer 10 performs a process of fitting to change the thickness, parameters of a dispersion formula and the like so that a difference between a model spectrum ($\Psi_M(\lambda_i)$, $\Delta_M(\lambda_i)$) obtained theoretically from the formed model and a measured spectrum ($\Psi_E(\lambda_i)$, $\Delta_E(\lambda_i)$) obtained from the measurement result obtained by the ellipsometer 1 is decreased. It should be noted that values in the model are changed and set as a result of the fitting and the values to be changed include the volume fraction of voids or any other parameters. The following expression (4) is applied as a dispersion formula in this embodiment:

$$\varepsilon = \varepsilon_\infty + \frac{(\varepsilon_S - \varepsilon_\infty)\varpi_t^2}{\varpi_t^2 - \varpi^2 + i\Gamma_0\varpi} + \frac{\varpi_P^2}{-\varpi^2 + i\Gamma_D\varpi} + \sum_{j=1}^{2} \frac{f_j \varpi_{oj}^2}{\varpi_{oj}^2 - \varpi^2 + i\gamma_j\varpi} \quad (4)$$

In the expression (4), $\in$ on the left side represents a complex dielectric constant, $\in_\infty$ and $\in_s$ represent dielectric constants, $\Gamma_0$, $\Gamma_D$ and $\gamma_j$ represent damping factors, and $\omega_{oj}$, $\omega_t$ and $\omega_p$ represent angular frequencies (oscillator frequency, transverse frequency, plasma frequency). It should be noted that $\in_\infty$ is a dielectric constant at a high frequency (high frequency dielectric constant) and $\in_s$ is a dielectric constant at a low frequency (static dielectric constant).

In the case of this embodiment, calculation is performed in a manner that a void volume fraction V in the layer of the model is set in a range between 60% and 90%, fitting is applied to parameters $\in_s$, $\omega_t$ and $\Gamma_0$ in the second term of the dispersion formula of the expression (4), known values are used as the other parameters, $\in_\infty$ in the first term is set to be "1", and the third term and the fourth term are set to be "0". The thickness and other parameters can be obtained as a result of fitting, and a complex dielectric constant $\in$ of the material can be obtained from the parameters of the dispersion formula using the expression (4). It should be noted that the complex dielectric constant $\in$ (corresponding to $\in(\lambda)$) and the complex refractive index N (corresponding to N($\lambda$)) have a relation of the following expression (5).

$$\in(\lambda) = N^2(\lambda) \quad (5)$$

Regarding the content of fitting, assuming that T measurement data pairs in a case of measurement of the sample S by the ellipsometer 1 are Exp (i=1, 2, . . . , T) and calculation data pairs of T models are Mod (i=1, 2, . . . , T), the mean square error $\chi^2$ on the least squares method using $\sigma_i$ as the standard deviation is obtained by the following expression (6) since the measurement error is to be normally distributed. It should be noted that P is the number of parameters. When the value of the mean square error $\chi^2$ is small, the coincidence between the measurement result and the formed model is large and the smallest value of the mean square error $\chi^2$ obtained by comparing a plurality of models corresponds to the best model.

$$\chi^2 = [1/(2T - P)]\sum_{i=1}^{T}(Exp_i - Mod_i)^2/\sigma_i^2 \quad (6)$$

Figure 4:
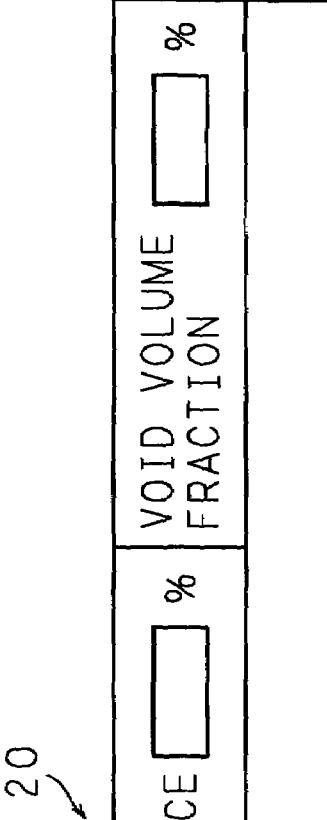

A sequence of steps to be performed by the computer 10 described above are defined in a computer program stored in the storage unit 11b, and steps programmed in this computer program includes a process to display a menu 20 for inputting and setting the thickness, the void volume fraction or other parameters as items of conditions of a model to be formed corresponding to physical properties of the sample on the screen of the display 12 as shown in FIG. 4. It should be noted that in this embodiment the ratio of a substance M forming the film S2' of FIG. 2B can be automatically set when the void volume fraction for the film S2' is set and the void volume fraction for the film S2' can be automatically set when the volume fraction of the substance M in the film S2' is just set. Accordingly, for the film S2', either one value of the void and the substance M constituting the film is set. For example, when the volume fraction of the substance M of the film S2' is set to be 30%, the void volume fraction of the film S2' is automatically set to be 70%.

Figure 5:
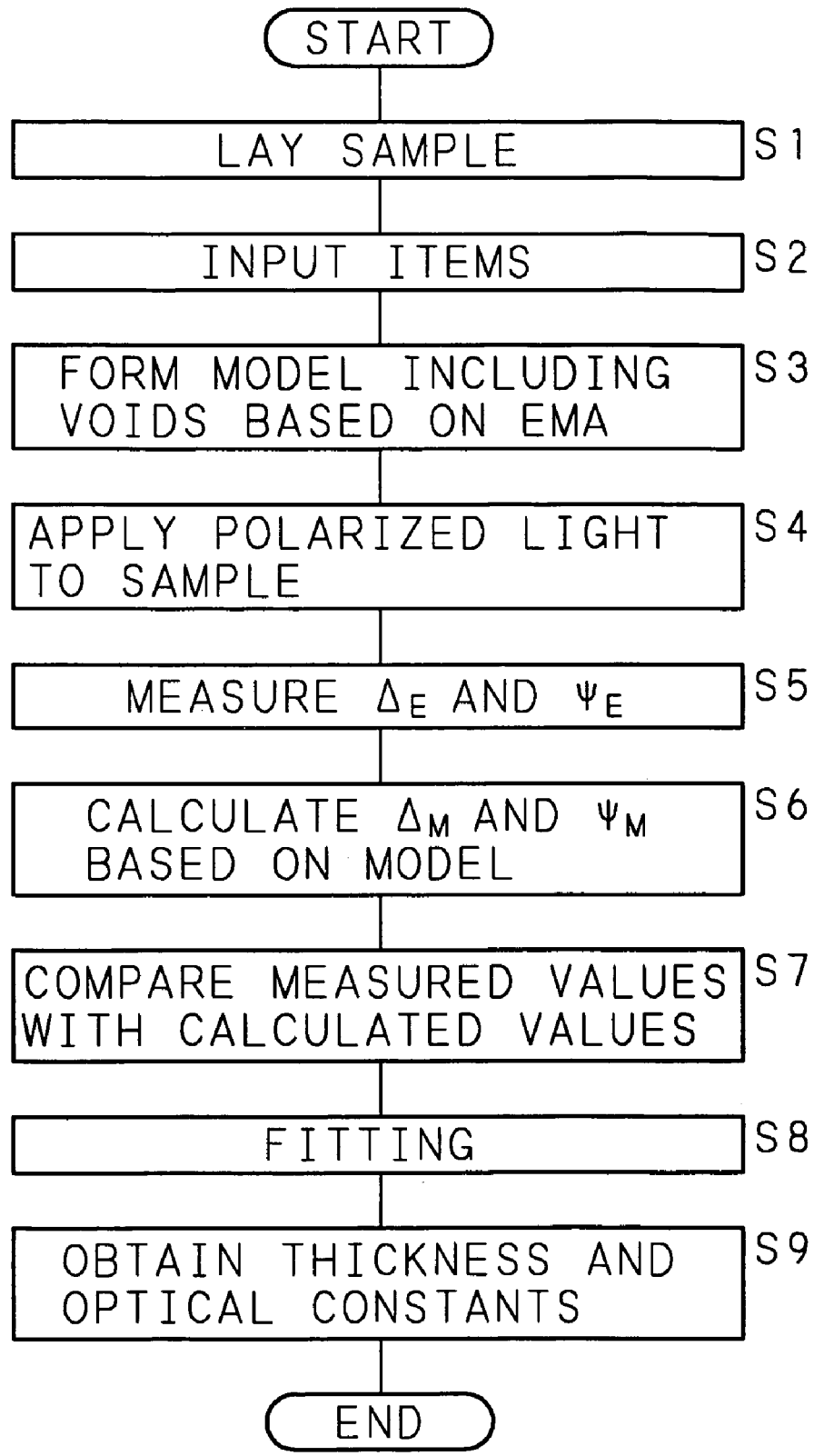
FIG. 5 is a flow chart showing a process according to the sample analysis method according to the present invention.

The following description will explain a sequence of procedures of a sample analysis method according to the present invention, which uses the ellipsometer 1 and computer 10 constructed as described above, with reference to a flow chart of FIG. 5.

First, a sample S, in which a dielectric film having a dielectric constant equal to or larger than 50 is formed on a substrate, is laid on the stage 4 of the ellipsometer 1 (S1). Next, measurement point of the sample S, angle of incidence $\phi$, conditions (material of the substrate, thickness of the dielectric film, optical constant and the like) for formation of a model corresponding to the sample and the like are inputted into the computer 10 as items on analysis (S2). In the present invention, a value of a void is also inputted as the conditions, which is a value within a range between 60% and 90% (e.g. 70%). When conditions are inputted in this manner, a model (see FIG. 2B) provided with a dielectric film including voids based on effective medium approximation, at a mixture ratio of the inputted value, is formed (S3).

Then, the ellipsometer 1 moves the light polarizer 3 and the light receiver 5 so that the angle of incidence $\phi$ and the angle of reflection $\phi$ become the inputted values, moves the stage 4 to apply polarized light to the sample (S4) and measures a phase difference $\Delta_E$ and an amplitude ratio $\Psi_E$ (S5). The computer 10 calculates a phase difference $\Delta_M$ and an amplitude ratio $\Psi_M$ from the formed model (S6) and compares the measured values obtained by the ellipsometer 1 with the calculated values based on the model (S7). Fitting is applied to the volume fraction of void of the dielectric film in the model, the volume fraction of the dielectric substance, the thickness and the parameters of the dispersion formula so that a difference between compared values becomes minimal (S8).

When the difference obtained by the least squares method using fitting falls below a desired value (becomes sufficiently minimal), the thickness, the optical constants and the like of the sample are obtained from the result thickness, parameters of the dispersion formula, void's optical constants and the volume fraction's value (S9). Thus, the present invention analyzes a sample by obtaining the thickness and the optical constants. It should be noted that parameters of the dispersion formula are associated with the dielectric substance component in the dielectric film, the dielectric constants of the dielectric substance component are obtained from the parameters, of dispersion formula and the dielectric constant on the entire dielectric film is calculated using effective medium approximation formula, using the dielectric constant of the dielectric substance component and the dielectric constant of the air component.

Next, an example of analysis to be made for a sample having a ferroelectric film formed therein, which uses a sample analysis method described above according to the present invention, will be explained. First, used is a sample in which a PZT film is formed on a Si (silicon) substrate having a Pt (platinum) film evaporated onto the surface thereof. It should be noted that PZT is a substance of mixture of lead titanate ($PbTiO_3$) and lead zirconate ($PbZrO_3$) and belongs to ferroelectric substances.

In this example of analysis, a model S' was formed corresponding to the sample, in which a film S2' including PZT (substance M) of 30% (volume fraction of 0.3) and void V of 70% (volume fraction of 0.7) based on effective medium approximation is formed on a Pt film S1' of a Si substrate in the structure illustrated in FIG. 2B, and the thickness d' of the film S2' was set to be 900 angstroms. It should be noted that, in formation of a model, a known reference was used for the Pt film on the substrate, and the following expression (7) of a Bruggeman effective medium approximation and the above expression (4) were used for the complex dielectric constant $\in$ of the PZT film. Used as the refractive index of void was the same value (approximately 1.003) as that of air.

$$f_a \frac{\varepsilon_a - \varepsilon}{\varepsilon_a + 2\varepsilon} + f_b \frac{\varepsilon_b - \varepsilon}{\varepsilon_b + 2\varepsilon} = 0, \quad (7)$$

where $fa+fb=1$.

In the expression (7), $\in$ represents an effective complex dielectric constant of the PZT film (film S2'), $\in_a$ represents a complex dielectric constant of PZT (material M: PZT component) in the PZT film, $\in_b$ represents a dielectric constant of void (air component) V in the PZT film, $f_a$ represents the volume fraction of PZT, $f_b$ represents the volume fraction of void and an effective complex dielectric constant of the entire PZT film was obtained based on the expression (7).

Figure 6A:
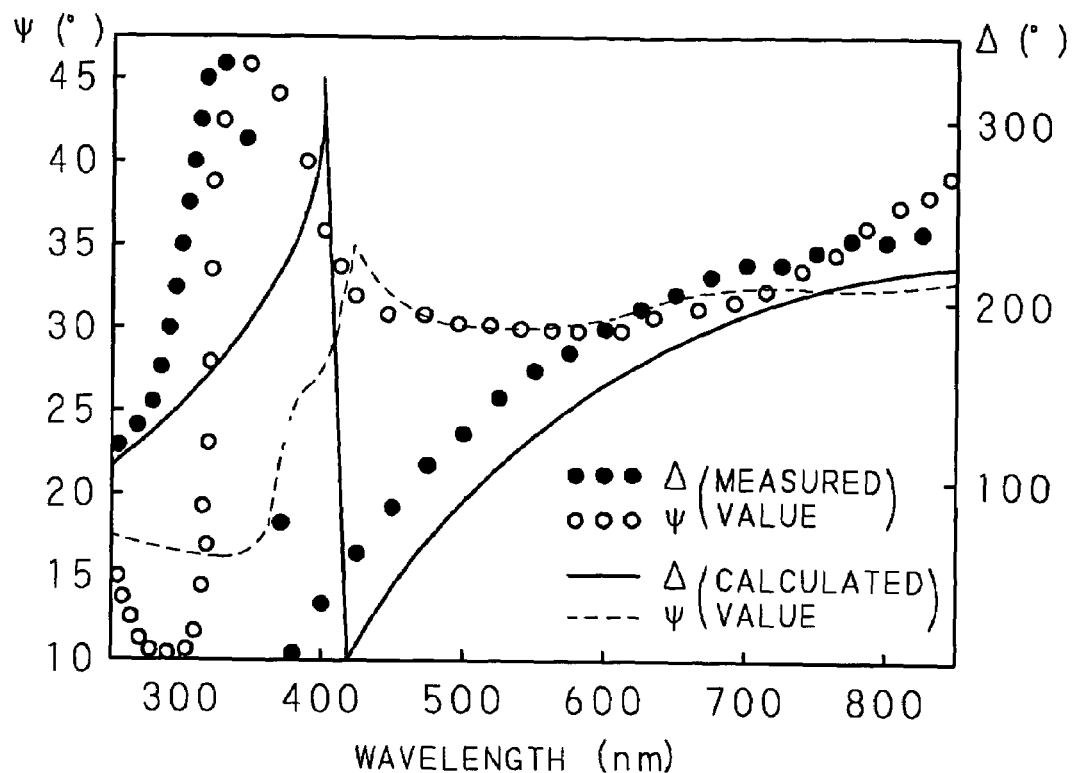
FIG. 6A is a graph showing the calculated value based on the model formed at first and the measured value obtained by the ellipsometer.

The graph in FIG. 6A shows the measured value for the above sample obtained by the ellipsometer 1 and the calculated value calculated theoretically from a model formed at first. As shown in the graph of FIG. 6A, when comparing the measured value with the calculated value, a clear difference exists between the calculated value and the measured value of the phase difference $\Delta$ and the amplitude ratio $\Psi$. Fitting was applied to the thickness d' of the film S2', the void volume fraction, the volume fraction of PZT and parameters of the dispersion formula of the expression (4) in such a state. It should be noted that fitting was applied only to $\in_s$, $\omega_t$ and $\Gamma_0$ of parameters of the expression (4) for the dispersion formula in this example of analysis.

Figure 6B:
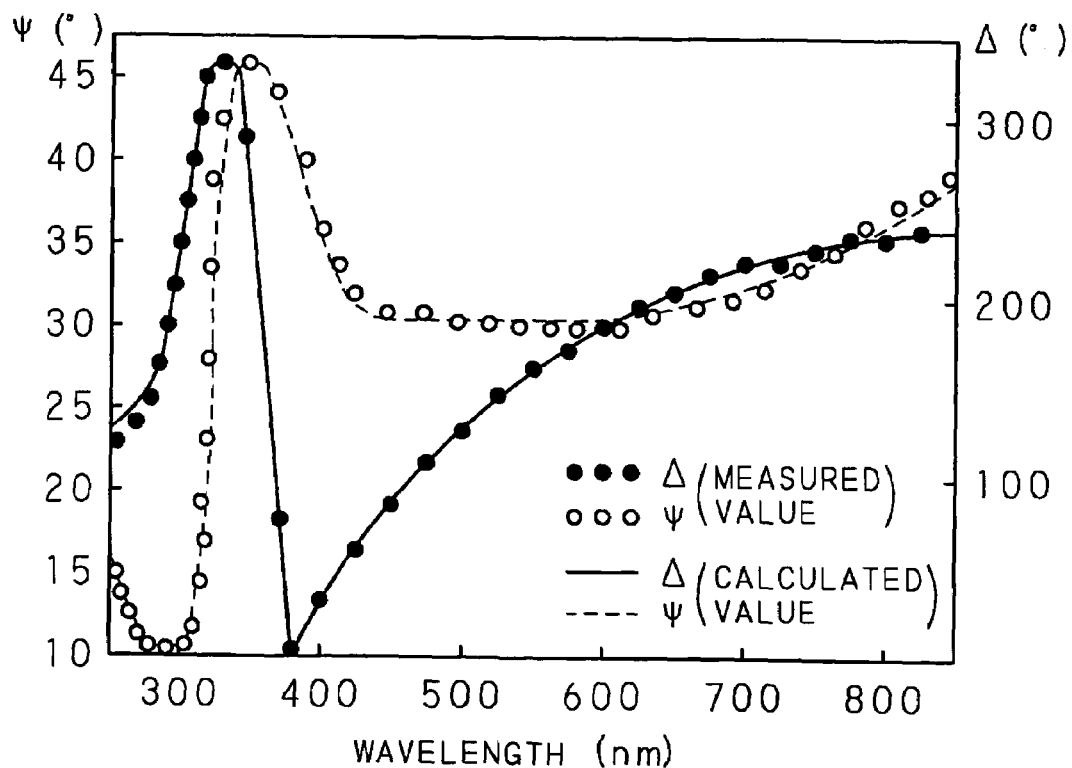
FIG. 6B is a graph showing the calculated value and measured value obtained after fitting.

FIG. 6B is a graph obtained after fitting and FIG. 7 is a diagram showing a result associated with fitting. As shown in the graph of FIG. 6B, the calculated value based on a model after fitting was substantially equal to the measured value obtained by the ellipsometer 1 even in a range between approximately 250 nm~400 nm and the value of the mean square error $\chi^2$ in the diagram of FIG. 7 was approximately 6.57, which was a sufficiently small value. Since a ratio of PZT with respect to the film S2' in this state is approximately 28.7%, it is found that void exists at a ratio of approximately 71.3%. The static dielectric constant ($\in_s$) of PZT component of the film S2' was approximately 372.79.

Figure 8:
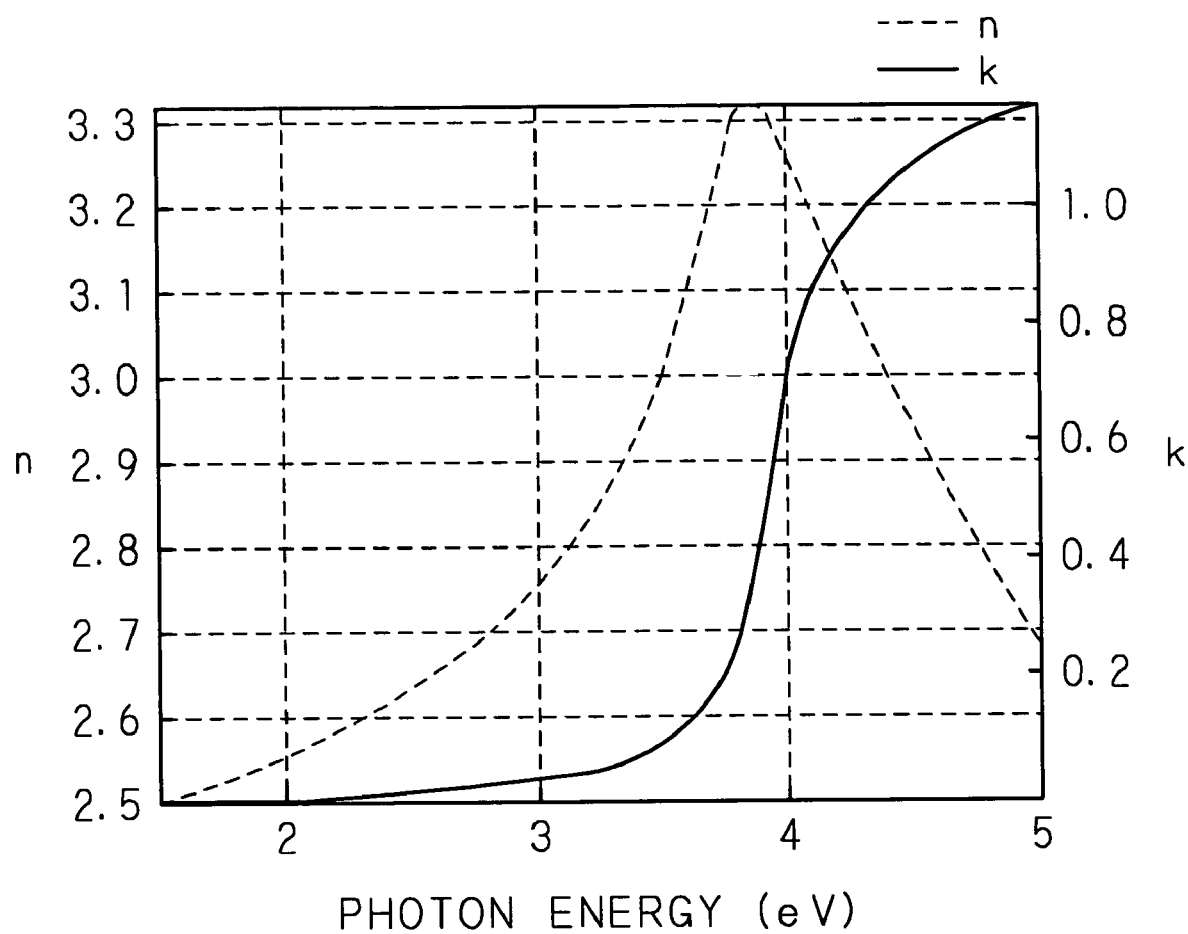
FIG. 8 is a graph showing the refractive index and the extinction coefficient.
Figure 9:
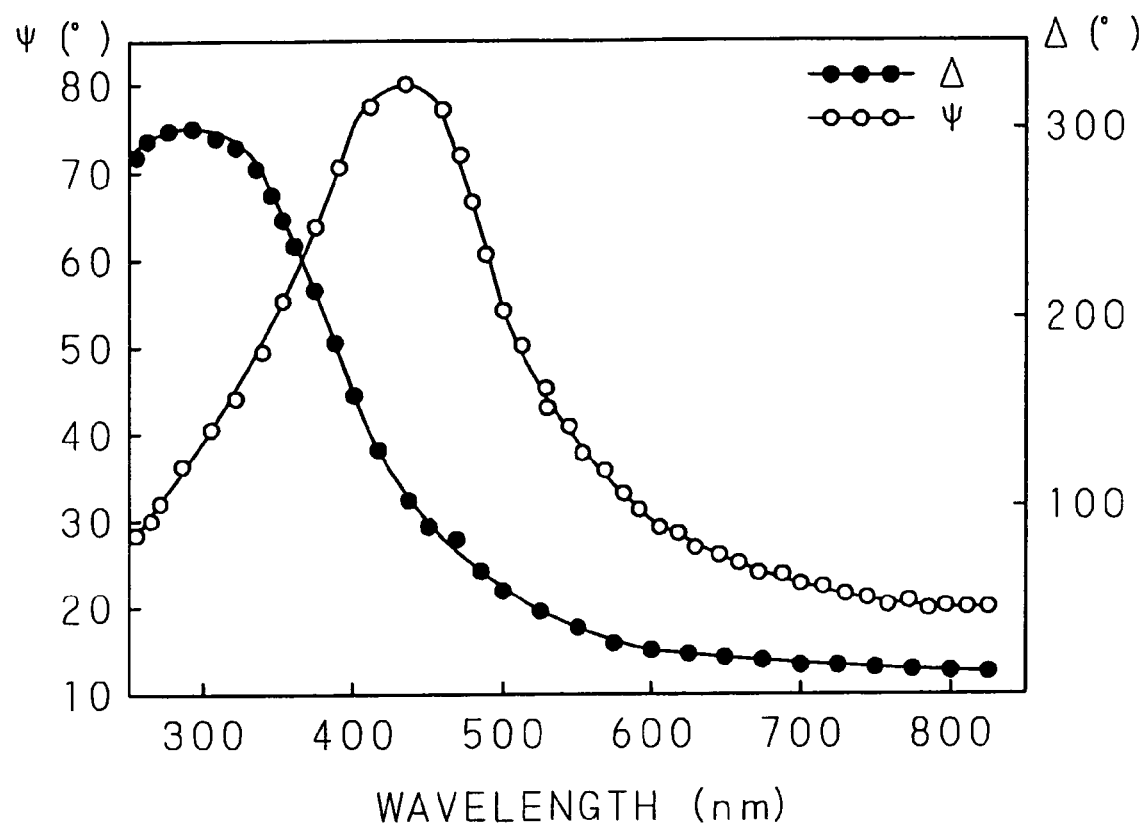
FIG. 9 is a graph showing the measurement result for silicon dioxide obtained by the ellipsometer.
Figure 10A:
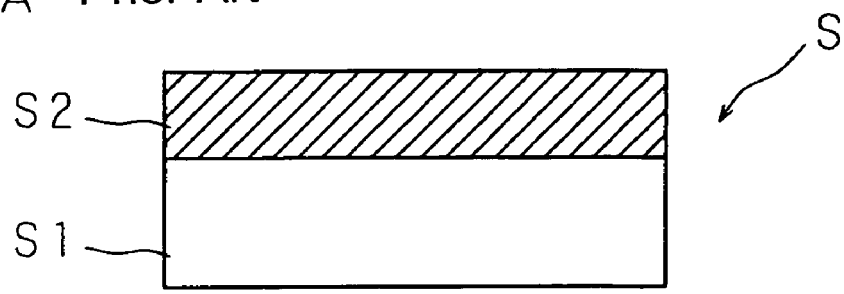
FIG. 10A is a schematic diagram showing the structure of the sample.
Figure 10B:
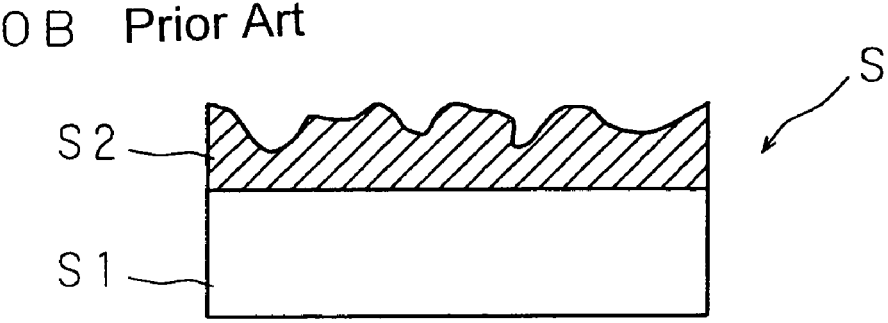
FIG. 10B is a schematic diagram of a sample having roughness on the film's surface.
Figure 10C:
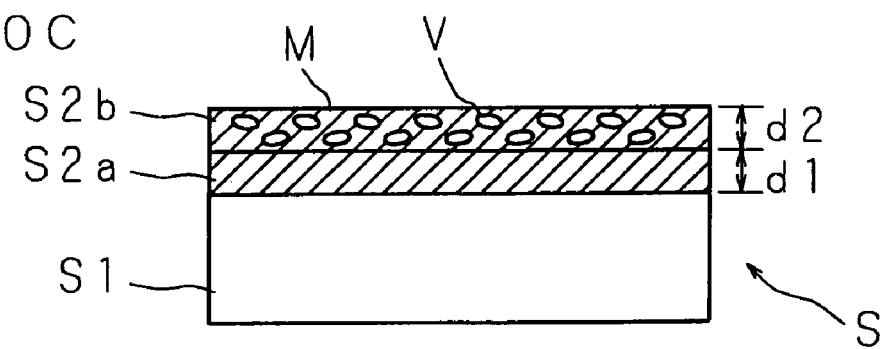
FIG. 10C is a schematic diagram showing the structure of a model including void based on effective medium approximation.

FIG. 8 is a graph showing the refractive index n and the extinction coefficient k of the PZT film calculated from a value specified by above fitting. Thus, with a sample analysis method according to the present invention, an analysis in a range under 400 nm which is impossible in the conventional technique can be made and a stable analysis in a range of 248 nm~826 nm can be realized. It should be noted that the abscissa axis of the graph in FIG. 8 uses as a unit a photon energy into which the wavelength can be converted (5 eV=approximately 248 nm).

Since the sample analysis method according to the present invention can analyze a sample in which a dielectric film having a dielectric constant equal to or larger than 50 based on electrical measurement is formed on a substrate, a sample having a $SrBi_4Ti_4O_{15}$ film can be analyzed preferably as well as a sample having a PZT film as described above, and a sample provided with a stack of dielectric films (having a dielectric constant equal to or larger than 50 based on electrical measurement) can be analyzed without trouble by applying the model structure illustrated in FIG. 2B to each film layer of each dielectric substance and performing the same calculation as that described above. Furthermore, though the expression (4) representing a dispersion formula and the expression (7) representing effective medium approximation equation were mentioned in the example, any known mathematical expression suitable for a sample, to be analyzed could be used in a suitable similar way.

It should be noted that a sample analysis method according to the present invention can be also used by applying fitting, separated to several stages instead of applying fitting to all the parameters at a time, as described above. Applying fitting to all the parameters at a time is suitable for a case where a dispersion formula for the sample is known, a case where a difference between the calculated value based on a model formed at first and the measured value obtained by the ellipsometer is small and the like. Applying fitting to each stage is suitable for a case where a dispersion formula of the sample is unknown, a case where a difference between the calculated value based on the formed model and the measured value obtained by the ellipsometer is large and the like.

In an example of applying fitting to each stage in the present invention, four kinds of models are first formed to respectively include void's volume fraction of 60%, 70%, 80% and 90% with respect to a film including voids, a value calculated based on each model is compared with the measurement result obtained by the ellipsometer 1, and a model (void's volume fraction) which gives the minimal difference is specified by the least squares method. Then an organized analysis is made for the specified void's volume fraction, by applying fitting to the thickness and the parameters of the dispersion formula. Furthermore, after specifying void's volume fraction in this manner, a plurality of thickness values are set, a model (thickness) which gives the minimal difference is specified similarly, and analysis can be made for the specified voids and thickness by fitting only the parameters of the dispersion formula.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A sample analysis method comprising the steps of:
   applying polarized light to a sample, in which a dielectric film having a dielectric constant equal to or larger than 50, based on electrical measurement, is formed on a substrate, by an ellipsometer;
   measuring a value of a difference between a polarization state of incident light and a polarization state of the light reflected from the sample;

forming, a model including void volume fraction between 60% and 90%, based on effective medium approximation, setting conditions corresponding to the sample;

calculating a value corresponding to the value of a difference in a polarization state measured by the ellipsometer, based on the formed model;

comparing the calculated value with the value of difference measured by the ellipsometer;

performing calculation using an effective medium approximation formula and a dispersion formula in the model, so that a difference between the compared values becomes minimal; and analyzing the sample based on a result of the calculation.

2. The sample analysis method according to claim 1, wherein the sample is provided with a stack of dielectric films having a dielectric constant equal to or larger than 50, based on electrical measurement, formed on the substrate, the step of measuring the value of the difference in a polarization state measures the value of difference between a polarization state of incident light and the light reflected from the sample for the stack of dielectric films and the step of forming the model includes void's volume fraction between 60% and 90%, based on effective medium approximation in each layer of the stack of dielectric films.

3. The sample analysis method according to claim 2, wherein the dispersion formula includes parameters describing a wavelength dependence of a dielectric constant of any dielectric film in the sample in which a stack of films is formed, corresponding to an optical measurement range, to analyze a dielectric constant in the optical measurement range, based on values of the parameters of the dispersion formula describing the dielectric constant.

4. The sample analysis method according to claim 3, wherein the dispersion formula is:

$$\varepsilon = \varepsilon_\infty + \frac{(\varepsilon_S - \varepsilon_\infty)\varpi_t^2}{\varpi_t^2 - \varpi^2 + i\Gamma_0 \varpi} + \frac{\varpi_P^2}{-\varpi^2 + i\Gamma_D \varpi} + \sum_{j=1}^{2} \frac{f_j \varpi_{oj}^2}{\varpi_{oj}^2 - \varpi^2 + i\gamma_j \varpi},$$

where $\varepsilon$: complex dielectric constant, $\varepsilon_\infty$: high frequency dielectric constant, $\varepsilon_s$: static dielectric constant $\Gamma_0$, $\Gamma_D$, $\gamma_j$: damping factors, and $\omega_{oj}$, $\omega_t$, $\omega_p$ angular frequencies (oscillator frequency, transverse frequency, plasma frequency).

5. The sample analysis method according to claim 4, wherein the step of performing calculation, changes values of $\varepsilon_s$ (static dielectric constant), $\omega_t$ (transverse frequency) and $\Gamma_0$ (damping factor), to decrease the difference between the compared values.

6. The sample analysis method according to claim 5, wherein the effective medium approximation formula is:

$$f_a \frac{\varepsilon_a - \varepsilon}{\varepsilon_a + 2\varepsilon} + f_b \frac{\varepsilon_b - \varepsilon}{\varepsilon_b + 2\varepsilon} = 0,$$

where $fa+fb=1$, $\varepsilon$: effective complex dielectric constant of a dielectric film, $\varepsilon_a$: complex dielectric constant of a dielectric substance in a dielectric film, $\varepsilon_b$: dielectric constant of void in a dielectric film, $f_a$: volume fraction of a dielectric substance, and $f_b$: void volume fraction.

7. The sample analysis method according to claim 1, wherein the dispersion formula includes parameters describing a wavelength dependence of a dielectric constant of any dielectric film in the sample in which a stack of films is formed, corresponding to an optical measurement range, to analyze a dielectric constant in the optical measurement range, based on values of the parameters of the dispersion formula describing the dielectric constant.

8. The sample analysis method according to claim 7, wherein the dispersion formula is:

$$\varepsilon = \varepsilon_\infty + \frac{(\varepsilon_S - \varepsilon_\infty)\varpi_t^2}{\varpi_t^2 - \varpi^2 + i\Gamma_0 \varpi} + \frac{\varpi_P^2}{-\varpi^2 + i\Gamma_D \varpi} + \sum_{j=1}^{2} \frac{f_j \varpi_{oj}^2}{\varpi_{oj}^2 - \varpi^2 + i\gamma_j \varpi},$$

where $\varepsilon$: complex dielectric constant, $\varepsilon_\infty$: high frequency dielectric constant, $\varepsilon_s$: static dielectric constant $\Gamma_0$, $\Gamma_D$, $\gamma_j$: damping factors, and $\omega_{oj}$, $\omega_t$, $\omega_p$: angular frequencies (oscillator frequency, transverse frequency, plasma frequency).

9. The sample analysis method according to claim 8, wherein the step of performing calculation, changes values of $\varepsilon_s$ (static dielectric constant), $\omega_t$ (transverse frequency) and $\Gamma_0$ (damping factor), to decrease the difference between the compared values.

10. The sample analysis method according to claim 8, wherein the effective medium approximation formula is:

$$f_a \frac{\varepsilon_a - \varepsilon}{\varepsilon_a + 2\varepsilon} + f_b \frac{\varepsilon_b - \varepsilon}{\varepsilon_b + 2\varepsilon} = 0,$$

where fa+fb=1, $\varepsilon$: effective complex dielectric constant of a dielectric film, $\varepsilon_a$: complex dielectric constant of a dielectric substance in a dielectric film, $\varepsilon_b$: dielectric constant of void in a dielectric film, $f_a$: volume fraction of a dielectric substance, and $f_b$: void volume fraction.

11. A sample analysis method comprising the steps of:

applying polarized light to a sample, in which a dielectric film having a dielectric constant equal to or larger than 50, based on electrical measurement, is formed on a substrate, by an ellipsometer;

measuring a value of a difference between a polarization state of incident light and a polarization state of the light reflected from the sample;

forming a plurality of models, including void volume fraction between 60% and 90%, based on effective medium approximation to have different void volume fraction, setting conditions corresponding to the sample;

calculating a value corresponding to the value of the difference in a polarization state measured by the ellipsometer for each model, based on the formed plurality of models;

comparing the calculated value for each model with the value of the difference measured by the ellipsometer respectively;

specifying a model, which gives a minimal difference between the calculated value and the value of the difference in a polarization state measured by the ellipsometer, from the plurality of models by comparison;

performing calculation using an effective medium approximation formula and a dispersion formula in the model, so that a difference between the calculated value for the specified model and the value of the difference in a polarization state measured by the ellipsometer becomes minimal; and analyzing the sample based on a result of the calculation.

12. The sample analysis method according to claim 11, wherein the sample is provided with a stack of dielectric films having a dielectric constant equal to or larger than 50, based on electrical measurement, formed on the substrate; the step of measuring the value of the difference in a polarization state measures the value of difference between a polarization state of incident light and the light reflected from the sample for the stack of dielectric films and the step of forming the model includes void's volume fraction between 60% and 90%, based on effective medium approximation in each layer of the stack of dielectric films.

13. The sample analysis method according to claim 12, wherein the dispersion formula includes parameters describing a wavelength dependence of a dielectric constant of any dielectric film in the sample in which a stack of films is formed, corresponding to an optical measurement range, to analyze a dielectric constant in the optical measurement range, based on values of the parameters of the dispersion formula describing the dielectric constant.

14. The sample analysis method according to claim 11, wherein the dispersion formula includes parameters describing a wavelength dependence of a dielectric constant of any dielectric film in the sample in which a stack of films is formed, corresponding to an optical measurement range, to analyze a dielectric constant in the optical measurement range, based on values of the parameters of the dispersion formula describing the dielectric constant.

15. The sample analysis method according to claim 14, wherein the dispersion formula is:

$$\varepsilon = \varepsilon_\infty + \frac{(\varepsilon_S - \varepsilon_\infty)\varpi_t^2}{\varpi_t^2 - \varpi^2 + i\Gamma_0\varpi} + \frac{\varpi_P^2}{-\varpi^2 + i\Gamma_D\varpi} + \sum_{j=1}^{2} \frac{f_j \varpi_{oj}^2}{\varpi_{oj}^2 - \varpi^2 + i\gamma_j\varpi},$$

where $\varepsilon$: complex dielectric constant, $\varepsilon_\infty$: high frequency dielectric constant, $\varepsilon_S$: static dielectric constant $\Gamma_0, \Gamma_D, \gamma_j$: damping factors, and $\omega_{oj}, \omega_t, \omega_p$: angular frequencies (oscillator frequency, transverse frequency, plasma frequency).

16. A sample analysis method comprising the steps of:

applying polarized light to a sample, in which a dielectric film having a dielectric constant equal to or larger than 50, based on electrical measurement, is formed on a substrate, by an ellipsometer;

measuring a value of a difference between a polarization state of incident light of the sample and a polarization state of the light reflected from the sample forming a plurality of models, including void volume fraction between 60% and 90%, based on effective medium approximation to have different void volume fraction, setting conditions corresponding to the sample;

calculating a value corresponding to the value of the difference in a polarization state measured by the ellipsometer for each model, based on the formed plurality of models;

comparing the calculated value for each model with the value of the difference measured by the ellipsometer respectively;

specifying a model, which gives a minimal difference between the calculated value and the value of the difference in a polarization state measured by the ellipsometer, from the plurality of models by comparison;

forming a plurality of models by setting a plurality of thickness values based on the specified model;

calculating a value corresponding to the value of the difference in a polarization state measured by the ellipsometer for each model, based on the formed plurality of models;

comparing the value calculated for each model with the value of the difference measured by the ellipsometer respectively;

specifying a model, which gives a minimal difference between the calculated value and the value of the difference in a polarization state measured by the ellipsometer, from the plurality of models by comparison;

performing calculation using an effective medium approximation formula and a dispersion formula in the model, so that a difference between the calculated value for the specified model and the value of the difference in a polarization state measured by the ellipsometer becomes minimal; and analyzing the sample based on a result of the calculation.

17. The sample analysis method according to claim 16, wherein the sample is provided with a stack of dielectric films having a dielectric constant equal to or larger than 50, based on electrical measurement, formed on the substrate, the step of measuring the value of the difference in a polarization state measures the value of difference between a polarization state of incident light and the light reflected from the sample for the stack of dielectric films and the step of forming the model includes void's volume fraction between 60% and 90%, based on effective medium approximation in each layer of the stack of dielectric films.

18. The sample analysis method according to claim 17, wherein the dispersion formula includes parameters describing a wavelength dependence of a dielectric constant of any dielectric film in the sample in which a stack of films is formed, corresponding to an optical measurement range, to analyze a dielectric constant in the optical measurement range, based on values of the parameters of the dispersion formula describing the dielectric constant.

19. The sample analysis method according to claim 16, wherein the dispersion formula includes parameters describing a wavelength dependence of a dielectric constant of any dielectric film in the sample in which a stack of films is formed, corresponding to an optical measurement range, to analyze a dielectric constant in the optical measurement range, based on values of the parameters of the dispersion formula describing the dielectric constant.

20. The sample analysis method according to claim 19, wherein the dispersion formula is:

$$\varepsilon = \varepsilon_\infty + \frac{(\varepsilon_S - \varepsilon_\infty)\varpi_t^2}{\varpi_t^2 - \varpi^2 + i\Gamma_0\varpi} + \frac{\varpi_P^2}{-\varpi^2 + i\Gamma_D\varpi} + \sum_{j=1}^{2}\frac{f_j \varpi_{oj}^2}{\varpi_{oj}^2 - \varpi^2 + i\gamma_j\varpi}, \quad 5$$

where $\in$: complex dielectric constant,
$\in_\infty$: high frequency dielectric constant, $\in_s$: static dielectric constant
$\Gamma_0$, $\Gamma_D$, $\gamma_j$: damping factors, and
$\omega_{oj}$, $\omega_t$, $\omega_p$: angular frequencies (oscillator frequency, transverse frequency, plasma frequency).

* * * * *